United States Patent
Ajdari et al.

(10) Patent No.: US 7,691,331 B2
(45) Date of Patent: Apr. 6, 2010

(54) MICROFLUIDIC FLOW DEVICE AND METHOD FOR USE THEREOF

(75) Inventors: Armand Ajdari, Paris (FR); Galder Cristobal, Bordeaux (FR); Mathieu Joanicot, Chatenay-Malabry (FR)

(73) Assignee: Rhodia Chimie, Aubervilliers (FR)

( * ) Notice: Subject to any disclaimer, the term of this patent is extended or adjusted under 35 U.S.C. 154(b) by 484 days.

(21) Appl. No.: 11/518,437

(22) Filed: Sep. 11, 2006

(65) Prior Publication Data

US 2007/0110631 A1 May 17, 2007

(30) Foreign Application Priority Data

Sep. 9, 2005 (FR) .................................... 05 09217
Jun. 15, 2006 (WO) ................ PCT/FR2006/001360

(51) Int. Cl.
*B01L 3/02* (2006.01)
*B01D 17/00* (2006.01)
*F15D 1/14* (2006.01)

(52) U.S. Cl. ........................ 422/100; 210/101; 137/834; 138/39

(58) Field of Classification Search .................. None
See application file for complete search history.

(56) References Cited

U.S. PATENT DOCUMENTS

| | | | |
|---|---|---|---|
| 6,090,251 A | 7/2000 | Sundberg et al. | |
| 6,136,272 A | 10/2000 | Weigl et al. | |
| 6,494,614 B1 | 12/2002 | Bennett et al. | |
| 6,558,960 B1* | 5/2003 | Parce et al. | 436/519 |
| 6,599,736 B2* | 7/2003 | McCaskill et al. | 435/288.5 |
| 6,838,232 B2 | 1/2005 | Nagasawa et al. | |
| 6,989,134 B2 | 1/2006 | Tonkovich et al. | |
| 7,016,560 B2 | 3/2006 | Ticknor et al. | |
| 2002/0197167 A1* | 12/2002 | Kornelsen | 417/53 |
| 2004/0136902 A1 | 7/2004 | Plath et al. | |
| 2005/0097951 A1* | 5/2005 | Hasselbrink et al. | 73/253 |
| 2005/0118070 A1 | 6/2005 | Griss et al. | |

FOREIGN PATENT DOCUMENTS

| | | |
|---|---|---|
| DE | 10213003 B4 | 8/2006 |
| EP | 1329765 A2 | 7/2003 |
| EP | 1525919 A | 4/2005 |
| WO | WO 98/55852 A1 | 12/1998 |
| WO | WO 02/083291 A1 | 10/2002 |
| WO | WO2004/038363 A2 | 5/2004 |

OTHER PUBLICATIONS

Kamholz et al., "Quantitative Analysis of Molecular Interaction in a Microfluidic Channel: The T-Sensor," Anal. Chem, Dec. 1, 1999, p. 5340-5347, vol. 71, No. 23, American Chemical Society.

* cited by examiner

*Primary Examiner*—Jill Warden
*Assistant Examiner*—Timothy G Kingan
(74) *Attorney, Agent, or Firm*—Buchanan, Ingersoll & Rooney P.C.

(57) ABSTRACT

A microfluidic flow device includes at least one flow channel flowing into a branch point, to which at least two branched channels are connected, and at least one linking channel interconnecting the two branched channels. The linking channel flows into each branched channel at a short-circuit point which is preferably located at less than half of the length of each branched channel.

21 Claims, 11 Drawing Sheets

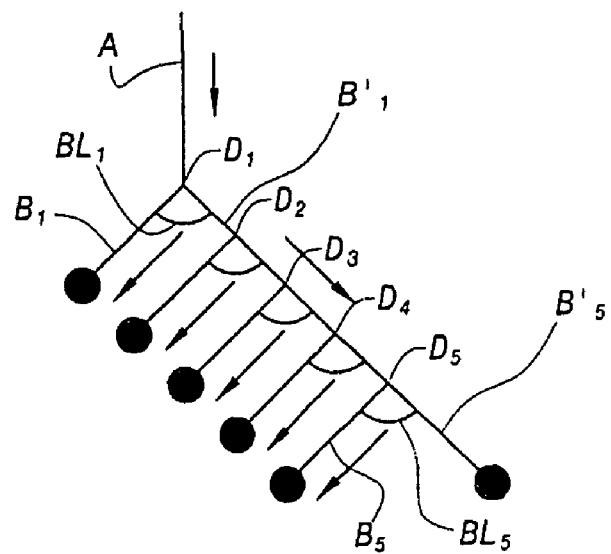
*Fig.* 6A
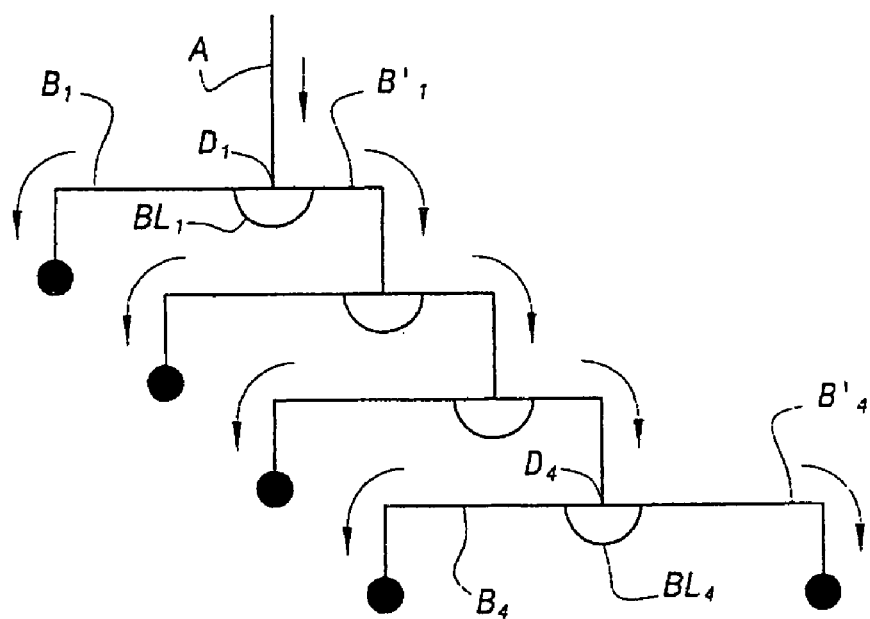
*Fig.* 6B

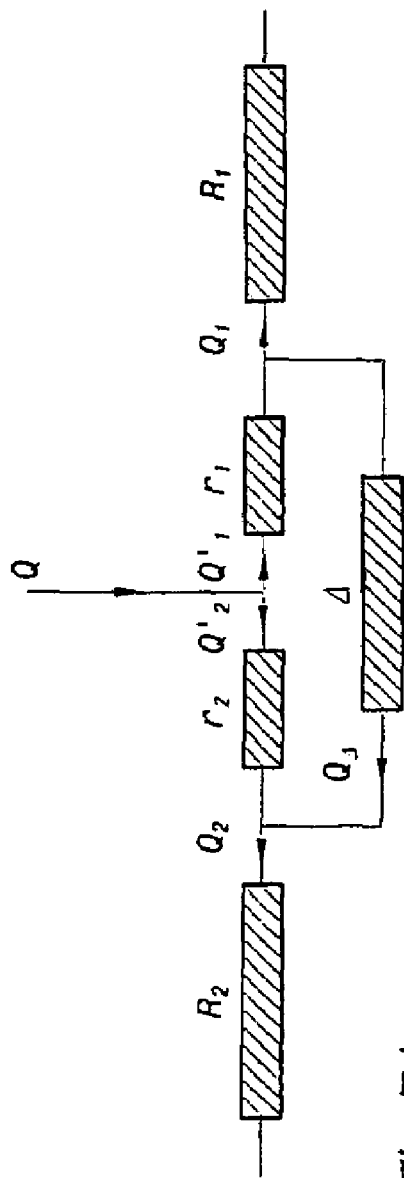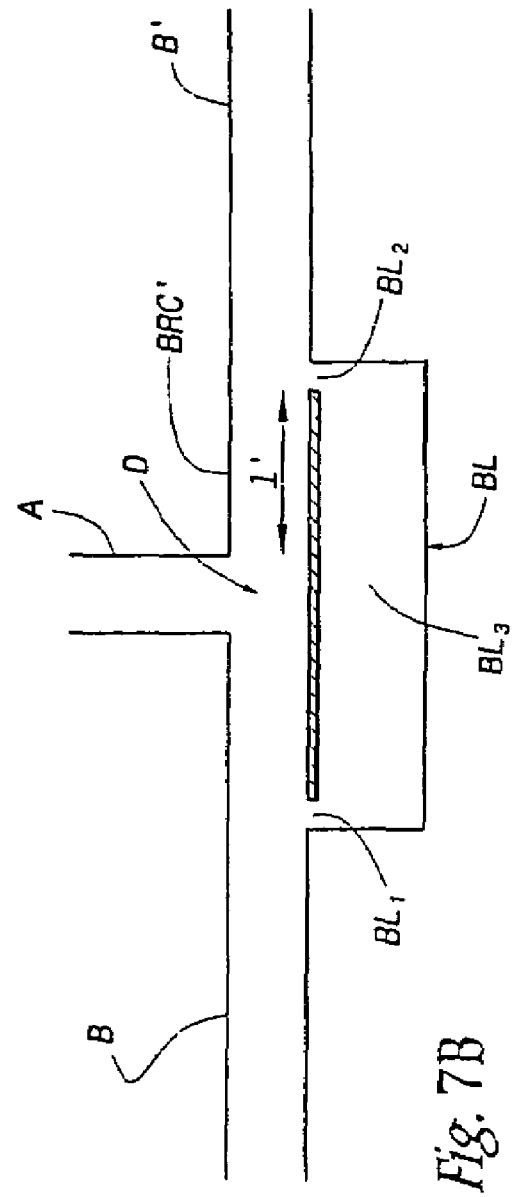
Fig. 7A
Fig. 7B

MICROFLUIDIC FLOW DEVICE AND METHOD FOR USE THEREOF

BACKGROUND

The present invention relates in particular to a microfluidic flow device. Conventionally, such a microfluidic flow device comprises at least one microchannel, for the flow of at least one fluid.

The characteristic dimension of each microchannel, as intended by the invention, is comprised between a few microns and 1 millimeter. Typically, this dimension causes a substantially laminar flow in the microchannel, with a Reynolds number lower than 1.

A microfluidic flow device is known from the article "Quantitative analysis of molecular interaction in a microfluidic channel: The T-sensor" (anal. Chem. 1999, 71, 5340-5347) which is referred to below as Yager et al. This flow device comprises two upstream channels, and a single downstream channel, which define a T shape. This publication describes the possibility of making a target fluid, and also a fluorescent indicator, flow in the downstream channel, in order to determine the concentration of this target fluid by measuring the fluorescence in a region of this channel, where interdiffusion occurs between the target fluid and the indicator.

Microfluidic techniques are used to provide access simply and/or rapidly and/or very accurately to chemical or physicochemical data. These techniques use fluid flows in channels. The fluids investigated are generally mixtures of chemical or biological compounds whereof the properties are analyzed at one or more points of the channel. The chemical or physicochemical history of the fluid evolves during their advance in the channels, by simple changes in a mixture (reaction kinetics, crystallization kinetics etc.) over time, and/or by mixing of several materials in the device. This makes it possible to perform analyses, investigate chemical or physicochemical or biological reaction mechanisms, design new materials at a small scale and investigate their properties, or even produce compounds.

To conduct these operations, fluid streams can be handled in channels. For example, a stream can be divided into two streams which each undergo a different treatment and/or different analyses. Two streams can be combined to create or investigate reactions.

Microfluidic devices are known comprising branch points (or junctions) and in which flows are conducted.

Plug flows (or "drops" or "plugs") are known in carrier fluids, like those described in WO2004038363, and devices for implementing such flows.

A need exists to improve the handling of the streams in microfluidic devices. A need exists in particular to improve the handling of plug streams, for example to distribute them better in various channels, and/or to merge various plugs thereby creating reaction mixtures, and/or to arrange and sort families of plugs and/or to ensure that they reach the destinations in the channels for which they are intended.

In particular, in general, a constant need exists in the industry to develop new products, having new properties, for example new chemical compounds or new compositions comprising new chemicals and/or new combinations thereof. The physical and/or chemical conversions of the products are important properties for many applications, which very often should be tested in Research and Development processes. A need exists for methods and installations for accelerating the Research and Development processes, for example to test a larger number of products and/or to conduct the tests on smaller quantities of products, and/or to conduct the tests more rapidly.

SUMMARY

This being said, the invention proposes to answer at least one of the needs described above.

For this purpose, the object of the invention is a microfluidic flow device which comprises:
  at least one flow channel, flowing into a branch point, to which at least two branched channels are connected, and
  at least one linking channel connecting the two branched channels,
  the linking channel flowing into each branched channel at a short-circuit point.

According to other features of the invention:
  the microfluidic flow device comprises said at least one flow channel, flowing into said branch point, to which at least said two branched channels, with respective lengths, are connected, and said at least one linking channel connecting the two branched channels, with the linking channel flowing into each branched channel at said short-circuit point which is located at less than half of the length of each branched channel;
  the device comprises a plurality of branch points, at least one of the branched channels of a first branch point flowing into a second branch point to which at least two branched channels are connected, the branched channel extending between the two branch points constituting a branched channel of the first branch point and the flow channel of the second branch point;
  the device comprises a linking channel connecting the two branched channels of the second branch point, flowing into each branched channel of the second branch point at a short-circuit point located at less than half of its length from each branched channel;
  the device comprises at least one parent flow channel, dividing into a first branch point and at least two $1^{st}$ order branched channels, whereof at least one is divided at a second branch point into at least two $2^{nd}$ order branched channels, at least one order branched channel being divided at an $n^{th}$ branch point into at least two $n^{th}$ order branched channels, n being greater than or equal to 2, preferably to 4, and preferably to 7;
  each $i^{th}$ order branch point, where i=1 to n, is associated with one $i^{th}$ order linking channel;
  the channels constitute a tree structure like system, the tree structure being symmetrical or asymmetrical;
  the flow channel and the branched channels constitute a symmetrical tree structure like system;
  the flow channel and the branched channels constitute an asymmetrical tree structure like system;
  the linking channel is provided with means for locally reducing its cross section;
  the linking channel comprises studs partially plugging the fluid inlet into said channel;
  the device comprises, preferably upstream of the flows, means for generating mobile fluid (s) plugs, particularly drops, separated by a carrier fluid, the plug fluid and the carrier fluid being immiscible;
  it is a divergent device, the flow channel being connected to a fluid inlet, the branched channels being connected to fluid outlets;
  the flow channel is connected to said plug generating means;

it is a convergent device, the flow channel being connected to a fluid outlet, the branched channels being connected to fluid inlets;

at least one of the branched channels, preferably at least both, is/are connected to the plug generating means.

A further subject of the invention is a method for sending or controlling material streams, preferably for handling plugs, preferably in a network, comprising the following steps:

introducing a fluid at at least one inlet of the device as defined above, and creating a fluid flow, divergent or convergent, through the flow channel and the branched channels.

According to other features of the invention:

the fluid comprises mobile fluid(s) plugs, or drops or dispersed entities, separated by a carrier fluid, the plug fluid and the carrier fluid being immiscible;

the plugs in the fluid upstream of the branch point are spaced at regular intervals;

the fluid is introduced at an inlet connected to the flow channel, the fluid flow comprising the plugs and the carrier fluid in the channel is a divergent flow from the fluid inlet in the flow channel to the branch point, and from the branch point to the branched channels, at the branch point the plugs:

are distributed at a substantially uniform rate in one branched channel then to the other, preferably at a rate of 1 then 1, or optionally, at a different rate, for example 1 then 2, are divided into two divided plugs, preferably at a substantially uniform rate, and/or coalesce with at least one of the next plugs;

two fluids comprising plugs, identical or different, are introduced at two inlets each connected to a branched channel, the fluid flow comprising the plugs and the carrier fluid in the channel is a convergent flow, from the fluid inlet in the branched channels to the branch point, and from the branch point to the flow channel, at the branch point at least one plug from a branched channel coalesces with at least one plug from the other branched channel;

the method is implemented in operations for preparing or creating materials ("material engineering"), and/or for analyzing, for measuring properties;

the plugs in the flow channel comprise a mixture of compounds, preferably mixed upstream of the plug formation, or during the plug formation in a convergent device, and/or mixed in the branch points during a coalescence.

BRIEF DESCRIPTION OF DRAWINGS

The invention will now be described with reference to the drawings appended hereto, provided only as nonlimiting examples, in which:

FIGS. 6A and 6B are front views, similar in particular to FIG. 4, showing two embodiments of a flow device according to the invention, forming a balanced asymmetrical tree structure;

FIG. 7A is an electrical diagram, whereas FIG. 7B is a front view, showing part of the flow device according to the invention, which is similar hydrodynamically to this electrical diagram;

DETAILED DESCRIPTION OF PREFERRED EMBODIMENTS

Figure 1:
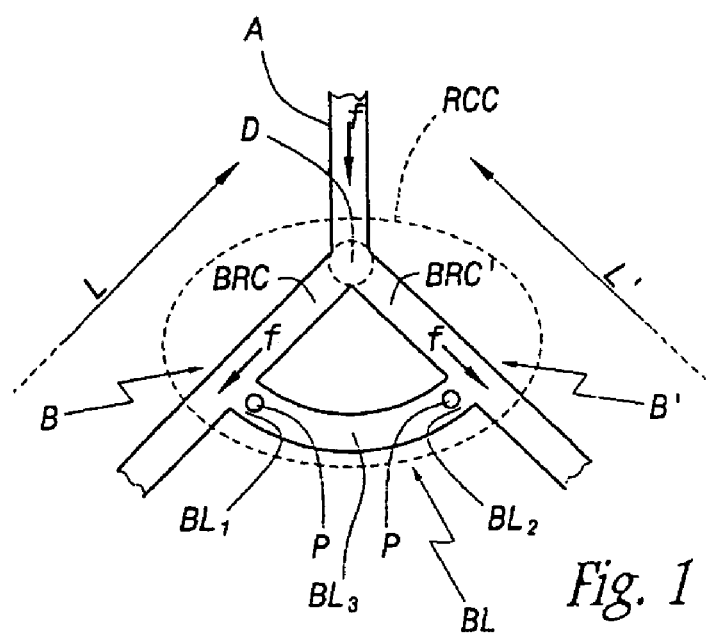
FIG. 1 is a front view, partially showing. a microfluidic flow device according to the invention.

FIG. 1 shows a microfluidic flow device according to the invention, which comprises first a body, forming a plate, which is not shown in the drawings.

This plate can be prepared in a manner known per se from poly (dimethylsiloxane), or PDMS. Various microchannels are etched into this plate, also conventionally. This plate has a typical length of 75 mm, a typical width of 50 mm, and a typical thickness of 1 mm. Furthermore, the various microchannels mentioned above have a typical cross section of between a few microns and one millimeter, particularly close to 50 microns. Another advantageous value of the cross section is close to 150 microns.

A flow channel A can therefore be observed, placed at the top of FIG. 1, in the bottom of which a branch point D is provided. Below are two branched channels B and B', which are connected by a linking channel BL.

Two studs P, forming obstacles, are provided close to the intersection of the linking channel BL and each of the branched channels B and B'. This linking channel BL can thereby be divided into three sections, that is first two end sections $BL_1$ and $BL_2$, whereof the cross section is low. Furthermore, a median portion $BL_3$ is observed, whereof the cross section is again wider.

In the context of the invention, a flow channel A is a channel suitable for comprising a single stream which is divided into two separate streams or which issues from two separate streams. In divergent operating mode, the flow channel A is a channel upstream of the branch point D. In convergent operating mode, the flow channel A is downstream of this branch point.

A "branch point" or "junction" or "node", or "branch", or "tree structure point", means a space into which at least three channels flow. The branch point may, for example, have a T or Y shape, more or less flared.

At a branch point, an upstream channel can thereby give rise to at least two downstream channels. This is referred to as divergent operation or flow.

Alternatively, at a branch point, at least two upstream channels can give rise to a single downstream channel. This case is referred to as convergent operation or flow.

The branched channels B and B' are channels intended each to comprise a separate stream which is combined with the other or which issues from a single stream divided to produce separate streams. In divergent operating mode, the branched channels B and B' are downstream of the branch point. In convergent operating mode, the divided channels B and B' are upstream of the branch point.

A linking channel BL, or linking branch, is a channel connecting branched channels together, flowing into a branched channel B at a point of the length of this branched channel, called the short-circuit point PCC, and on the branched channel B', at a point of the length of this branched channel B', called the short-circuit point PCC'. The short-circuit points each denote a space where the linking channel flows into the branched channel. The short-circuit points are also referred to as "bypass points".

A short-circuit network branch BRC or BRC', or "short-circuit branch" or "short-circuited branch" or "bypass branch" or "short-circuit segment" or "bypass segment" means the segment of a branched channel B or B' extending from the branch point D to the point where the linking channel BL terminates, or the short-circuit point PCC or PCC'. The length of a short-circuit network branch (that is the length of the segment or "short-circuit length" or "bypass length") is defined as the length l for the branched channel B, respectively l' for the branched channel B'.

Figure 1A:
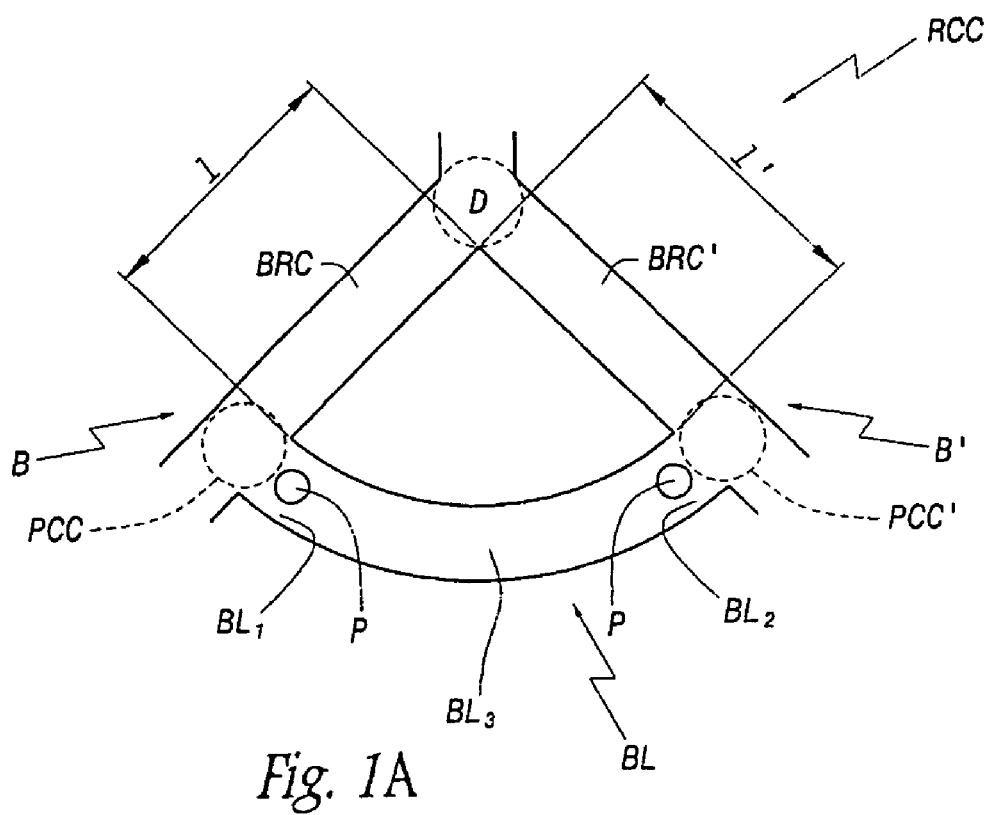
FIG. 1A is a front view, similar to FIG. 1, more particularly illustrating certain components of the device in FIG. 1.

As shown more particularly in FIG. 1A, a "short-circuit network" RCC or more simply "short-circuit" or "bypass", means all the channels or part of the channels comprising the branch point D, the linking channel BL, and the short-circuit network branches BRC and BRC' of the branched channels B and B'. Preferably, in the short-circuit network, there is a local symmetry for the parts relative to the branched channels B and B'. Thus l is generally equal to l'.

The length of the flow channel A and the lengths L and L' of the branched channels B and B' are defined as the lengths of the segments between the branch point D and a point where the streams are created or modified significantly, for example an inlet and/or outlet, a tank, a branch point upstream or downstream. Thus, in FIG. 1, such a point is not shown. In the case of divergent operating mode, the lengths are the length between the branch point and a downstream point such as another downstream branch point (for a tree structure like device, for example) or a flow interruption tank, or an outlet of the device.

By construction l<L, and l'<L'. Preferably, these lengths L or L' of the branched channels B and B' are significantly higher than the lengths l and l' of the short-circuit network branches BRC. and BRC'. In particular, the ratio L/l, or L'/l', is higher than 2, that is the short-circuit point PCC or PCC' is located at less than half of the length L or L' of each branched channel B or B'.

The microfluidic flow device according to the invention is suitable particularly for determining the parameters of a physical and/or chemical conversion.

Conversion means any type of interaction capable of occurring in a mixture of at least two components. In a nonlimiting manner, this conversion may be a chemical or physical reaction, such as, for example, any type of conventional chemical reaction, and also a crystallization or precipitation, or, inter alia, a modification of a liquid/vapor equilibrium. In general, in the context of the invention, such a conversion is likely to make use of chemical mechanisms, by exchange or joining of electrons, physical interactions or repulsions, such as hydrogen bonds, electrostatic interactions, steric attractions or repulsions, affinities for various hydrophilic and/or hydrophobic media, formulation stabilities, flocculations or even phase transfers, for example of the liquid/liquid, solid/liquid or gas/liquid type. In the context of the invention, the parameters of such a conversion are, in a nonlimiting manner, the chemical reaction kinetics in homogenous or heterogeneous medium, the conditions for obtaining an optimum yield for chemical reactions, enthalpies of reactions, time-related processes of chemical and physical reactions, and also solubility or even phase diagrams.

Figure 2:
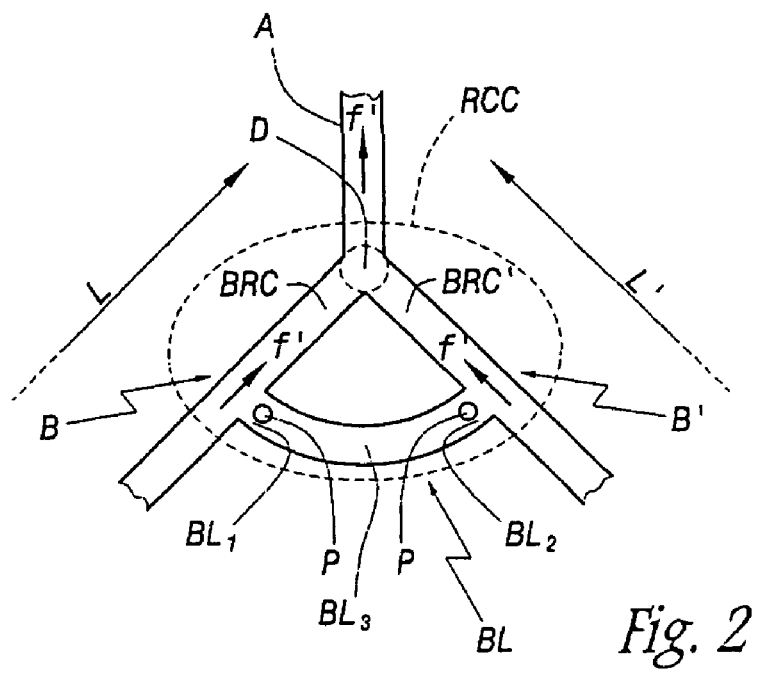
FIG. 2 is a front view, similar to FIG. 1, showing an alternative arrangement of the device in FIG. 1.

As stated above, the various fluids flowing in the device according to the invention are capable of advancing in respectively convergent and divergent modes, as shown in FIGS. 1 and 2.

Thus, in FIG. 1, the divergent flow of the fluids is materialized by the arrows f. In other words, the flow channel A is an upstream channel, which gives rise to two branched channels B and B' placed downstream. The single fluid flowing in the channel A is thus divided into two separate streams flowing into the channels B and B'.

FIG. 2 shows the alternative solution, of the convergent type, for which the fluid flow is materialized by the arrows f' with the understanding that the flow device is identical to that in FIG. 1. In this case, the branched channels B and B' are placed upstream, whereas the flow channel is placed downstream. The latter receives the flow of a single fluid, which issues from two separate streams flowing respectively in the channels B and B'.

Figure 3:
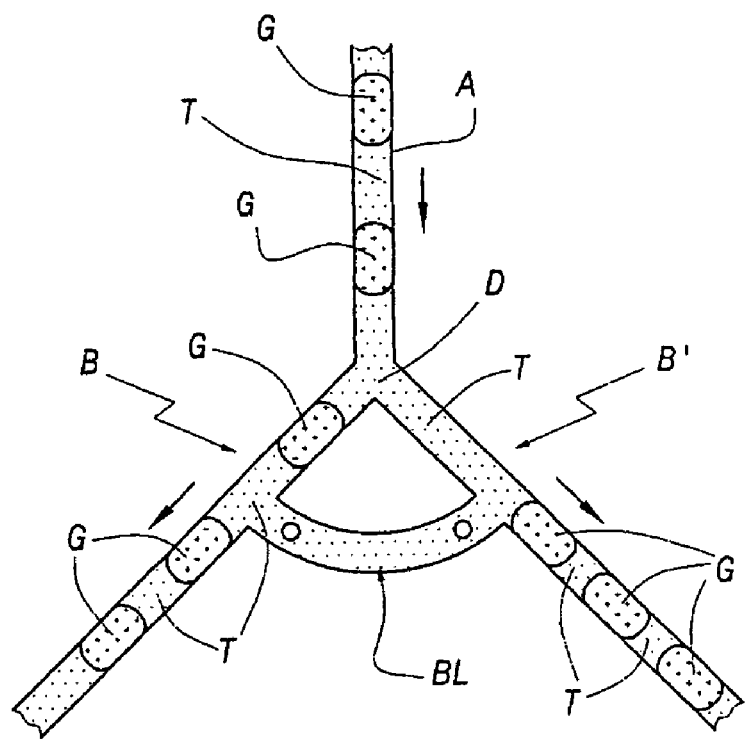
FIG. 3 is a front view, similar to FIG. 2, showing another alternative arrangement of the device according to the invention.

FIG. 3 shows one embodiment of the invention, that is a divergent type of flow, as defined above, of a fluid comprising a plurality of phases. This figure accordingly shows a succession of drops G, forming plugs, and sections T of a carrier phase which flow in the upstream flow channel A and then in the two downstream branched channels B and B'. These plugs are generated by plug generating means, which are, for example, those described in document WO-2004038363, included by reference in the present application.

Figure 3A:
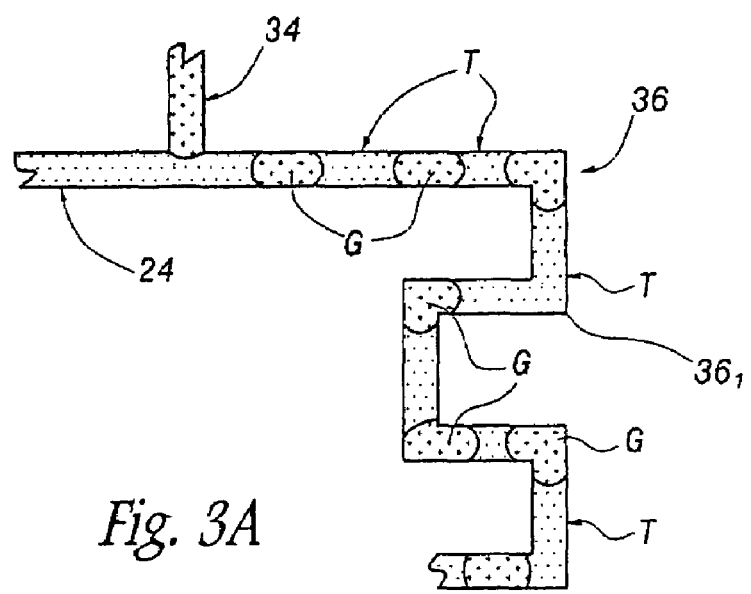
FIG. 3A is a front view, at a larger scale showing plug formation means, provided in the upstream part of the device according to the invention.

FIG. 3A shows another possibility of producing such plugs. It first shows an upstream channel 34, in which a mixture of two components flows, particularly reagents, which are intended to form drops G, or plugs. This mixture is fed from inlets not shown, downstream whereof intermediate microchannels extend, also not shown, which flow into the upstream microchannel 34. Owing to the very nature of the latter, in particular its dimensions, the two components flow therein substantially without undergoing any mixing. In fact, in this microchannel 34, mixing can only occur by molecular diffusion. Under these conditions, if this microchannel 34 is sufficiently short, the molecules of the two compounds do not have the time necessary to diffuse, so that the streams do not interpenetrate. However, it may be advantageous, as an alternative not shown, to add a neutral fluid in a manner known per se.

Furthermore, via another inlet, also not shown, a carrier liquid phase is introduced, which is immiscible with the abovementioned reagents. The flow rate of the two reagents is advantageously between 0.1 microliter/hour and 1000 microliters/hour, whereas the flow rate of the carrier phase is advantageously between 0.1 microliter/hour and 100 000 microliters/hour.

This liquid carrier phase flows in an auxiliary microchannel 24. Since these reagents are immiscible with the carrier phase, downstream of the junction between the microchannels 24 and 34, a succession of drops G is formed, constituting plugs or dispersed entities, whereof each is composed of a mixture of the two abovementioned components. Two successive drops are accordingly separated by a section T of the carrier phase.

As shown in FIG. 3A, the drops G occupy the entire cross section of a downstream microchannel 36, so that all the components, that is these drops and the carrier phase have the same speed. In this microchannel 36, the flow is therefore of the plug or piston type.

Upstream of the microchannel 36, the components of each drop are mixed very little, if at all. Then, as they advance, the drops G are subjected to modifications of their interior flow, thanks to the fold walls $36_1$, wherewith this microchannel 36 is provided in a manner known per se. The latter also flows into the flow channel A, so that, close to the branch point D, the components are properly mixed in each drop G.

In the context of the invention, the flow and branched channels are intended to receive the flow of a fluid, which may comprise several phases along these channels. Plugs or "drops" or "dispersed entities" are fluid phases flowing along the channels, substantially occupying the width of the channels, separated from one another by a carrier fluid immiscible with the plug fluid. For example, the carrier fluid may be a hydrophobic phase, the plug fluids being aqueous phases. The carrier fluid may be an aqueous phase, the plug fluids being hydrophobic phases. The fluid flowing in the channels may in particular be an alternate succession of plugs and sections of carrier fluid. Thus the fluid can be regarded as a continuous string of plugs.

If the succession is irregular or discontinuous, leaving spaces of carrier fluid alone and alternate succession spaces, this can be referred to as trains of plugs or trains of drops. The fluid may comprise several families of plugs. A family of plugs is defined as a set of plugs having the same source and/or identical compositions but capable of evolving by chemical, biological or physical chemical reaction. Thus the flow fluid in the channels may be an alternate succession of carrier fluid and plugs, the plugs themselves possibly defining a regular or irregular alternation of several families of plugs.

Alternation with one family of plugs: . . . -carrier-plug-carrier-plug-carrier-plug- . . .

Alternation with two families of plugs: . . . -carrier-type 1 plug-carrier-type 2 plug- . . . carrier-type 1 plug-carrier-type 2 plug-carrier -type 1 plug- . . .

The arrangement described with reference to the preceding figures comprises a single branch point, from which extend two branched channels, called $1^{st}$ order, referenced numerals $B_1$ and $B'_1$ in FIG. 4, the branch point and the linking channel having the reference numerals $D_1$ and $BL_1$. As this figure shows, it can be provided that each $1^{st}$ order branched channel flows into a corresponding branch point, called $2^{nd}$ order, which is denoted $D_2$ or $D'_2$. In this case, two $2^{nd}$ order branched channels, referenced $B_2$ to $B'''_2$, extend from each $2^{nd}$ order branch point, it being understood that two additional linking channels $BL_2$ and $BL'_2$ connect each pair of $2^{nd}$ order branched channels.

In a manner not shown, it can be provided that each $2^{nd}$ order branched channel is itself divided into two 3rd order branched channels, which are connected by an additional linking channel. Iteratively, a symmetrical tree structure can be produced, whereof the channels of a maximum order have an order above 4, preferably above 7.

Figure 4:
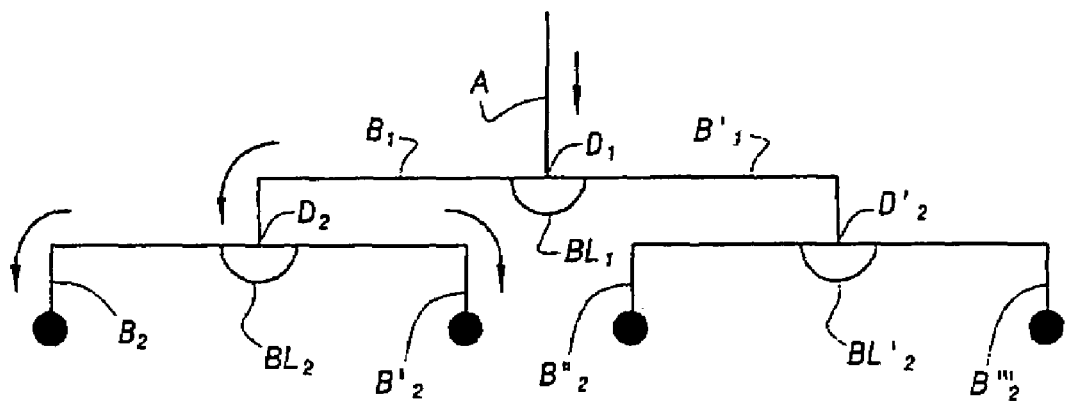
FIG. 4 is front view, similar to the preceding figures, showing a flow device according to the invention, having a symmetrical tree structure.

The arrangement of this FIG. 4 is symmetrical about a median vertical axis of the sheet. In the context of the invention, the term "symmetrical" means that the pattern formed by these channels is symmetrical, particularly about an axis. Preferably, the transversal dimension of these channels is also symmetrical and, even more preferably, the nature of the fluid flows in these channels is also symmetrical.

According to the invention, it can also be provided to produce an asymmetrical type of tree structure, due to the geometric nature and/or the transversal dimensions of the various channels. In other words, an arrangement may be asymmetrical in the context of the invention even when the various branched channels are geometrically symmetrical about a median vertical axis, insofar as the cross sections of the channels of the same order are different.

It has been found that at each branch point (or junction), an equal partition of the flow rates is favorable. It has been found that the behavior of the plug is often uncontrolled, insofar as they always follow the highest flow rates. If, at a junction, this equipartition is absent, the plugs will follow the highest flow rate and the chances of observing plugs in the final channels of the system and of obtaining long residence times are reduced.

In the case of a symmetrical tree structure, like the one in FIG. 4, the equipartition can be provided by the symmetry of the system. However, the distribution of the plugs remains difficult to control. To make an asymmetrical device operate, it has been found that an equipartition, which is desirable, can be obtained by balancing the tree structure. This balancing is in fact similar to that of an electrokinetic circuit when the resistances of the issuing branches are equalized at a node.

Figure 5:
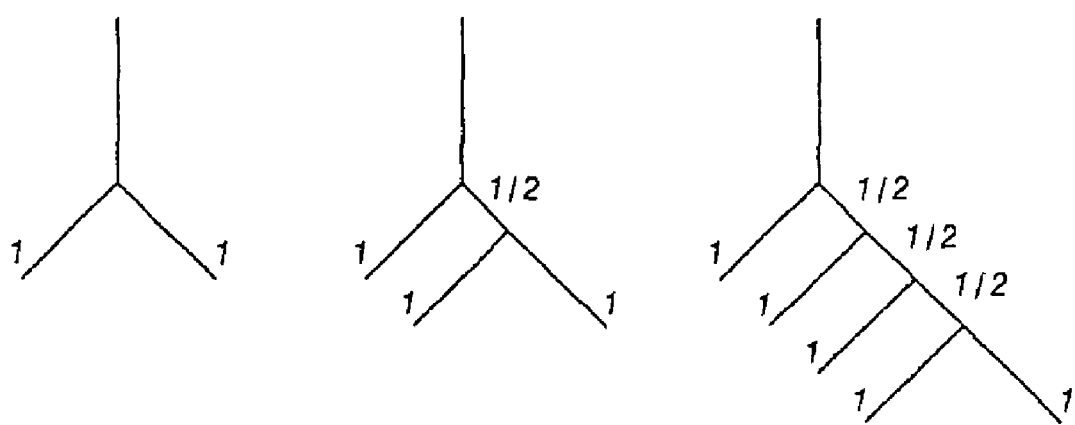
FIG. 5 is a schematic view, showing the arrangement of a balanced asymmetrical tree structure of a device according to the invention.

The construction of a balanced asymmetrical tree structure is obtained by the following principle: all the outlets have an identical fixed length and all the nodes are interconnected by channels of half length (see FIG. 5). In this figure, the lengths are schematically assigned the reference numerals ½ or 1.

The residence times obtainable by such a device can be evaluated, and compared with a linear channel.

At the pth outlet, the residence time reached is given by the following formula:

$$t_p = \sum_{q=1}^{p-1} \left( \frac{L/2}{v/2^q} \right) + \frac{L}{v/2^p}$$

$$= \frac{L}{v} \cdot \left( \sum_{q=1}^{p-1} (2^{q-1}) + 2^p \right)$$

$$= \frac{L}{v} \cdot (2^{p-1} - 1 + 2^p)$$

$$= (3 \cdot 2^{p-1} - 1) \cdot \frac{L}{v} \text{On}$$

It is observed that the residence times no longer vary linearly along the channel but exponentially, making it possible to reach long residence times without encountering problems of size. The following comparative table can also be compiled (Table 1):

TABLE 1

MAXIMUM RESIDENCE TIMES IN A LINEAR CIRCUIT AND IN AN
ASYMMETRICAL TREE STRUCTURE AND GAIN.

| Number of Intersections | 1 | 2 | 3 | 4 | 5 | 6 | 7 | 8 |
|---|---|---|---|---|---|---|---|---|
| Total length of the system | 2L | 7L/2 | 5L | 13L/2 | 8L | 19L/2 | 11L | 25L/2 |
| Maximum residence time for a linear circuit of this length | 2L/v | 7L/2v | 5L/v | 13L/2v | 8L/v | 19L/2v | 11L/v | 25L/2v |
| Residence time at the final outlet | 2L/v | 5L/v | 11L/v | 23L/v | 47L/v | 95L/v | 191L/v | 383L/v |
| Gain (ratio of maximum residence times) | 1 | 1.43 | 2.2 | 3.54 | 5.88 | 10 | 17.36 | 30.64 |

Advantage and Principle of the Bypass

The preceding arrangement, shown in FIG. 5, appears to ensure, at each intersection, an equal distribution of the total upstream flow rate between the two downstream branches if a single-phase system is examined.

However, it has been found that on two-phase systems, the equipartition is not always obtained, at least locally:

Each drop, or plug, actually behaves as a mobile hydrodynamic resistance. When, at a junction, a drop travels toward a branch of the tree structure, it increases the total resistance of this branch. The next drop should hence theoretically opt for the other branch, whereof the resistance is lower.

However, this ideal operation is difficult to obtain in reality for various reasons:

unmeasurable defects during fabrication can cause an imbalance between the hydrodynamic resistances of the two branches in parallel, fluctuations in the dynamics of the system (elasticity of the channels, capillary pressure at the outlet, etc.) may be another source of imbalance.

It has been found that, when the hydrodynamic resistances of the two branches are equal, the drops reaching the junction are not. distributed in a 1:1 arrangement into the two branches, but in a chaotic manner. The distribution of the drops takes place by trains of drops, generally random and irregular.

It has accordingly been found advisable to find a system which amplifies the increase in hydrodynamic resistance caused by the arrival of a drop in a branch so that the next drop selects the other branch.

Starting with this idea, the system of the invention which is called "bypass" has the role, for example, of accentuating the influence of the last drop passed, so that it repels the next to the other branch.

FIG. 6A shows an asymmetrical device, as obtained according to the construction in FIG. 5, which integrates linking channels according to the invention. Thus, at each branch point, such a linking channel is found, connecting two branched branches of the same order. One accordingly finds the flow channel A, placed here upstream, various branch points $D_1$ to $D_5$, various $1^{st}$ to $5^{th}$ order branched channels, $B_1$ and $B'_1$ to $B_5$ and $B'_5$, and linking channels $BL_1$ to $BL_5$.

FIG. 6B shows an alternative arrangement of the tree structure in FIG. 6A. Thus in this FIG. 6B, the branched channels are not straight as in FIG. 6A, but roughly have an L shape. As previously, two branched channels of the same order are connected by one respective linking channel.

To better understand how the system of the invention can operate, use may be made of an analogy with electrokinetics. FIG. 7A shows an electrical equivalent of a microfluidic flow device according to the invention, shown in FIG. 7B.

The device in FIG. 7B, which corresponds to that in FIG. 1, has been modified in shape, in order to highlight the analogy with the electrical diagram in FIG. 7A. In this FIG. 7B, the flow channel A, branch point D, two branched channels B and B' are shown, and also the linking channel BL. Also shown are the three parts of the linking branch BL, that is, the two end sections $BL_1$ and $BL_2$, whereof the cross section is low, in order to prevent the passage of plugs like those shown in FIG. 3. The median portion $BL_3$ is shown lastly, whereof the cross section is again wider, in order to have a low hydrodynamic resistance. In this FIG. 7B, the length of the short-circuit network BRC' is also denoted l'.

If the mesh law is written for the circuit in FIG. 7A, we have:

$$-R_2 Q_2 - \Delta Q_\Delta + R_1 Q_1 = 0$$

or $$Q_\Delta = \frac{R_1 Q_1 - R_2 Q_2}{\Delta}$$

and $$r_1 Q'_1 - r_2 Q'_2 = -\Delta Q_\Delta$$

Moreover, the node law gives $Q_1 = Q_1' - Q_\Delta$ and $Q_2 = Q_2' + Q_\Delta$. Simple calculations of these four equations yield the expression of the ratio of the flow rates at the junction:

$$\frac{Q'_1}{Q'_2} = \frac{r_2 + \frac{\Delta R_2}{\Delta + R_1 + R_2}}{r_1 + \frac{\Delta R_1}{\Delta + R_1 + R_2}} = \frac{r_2(\Delta + R_1 + R_2) + \Delta R_2}{r_1(\Delta + R_1 + R_2) + \Delta R_1}$$

This shows that without branch point ($\Delta$ infinite), $$\frac{Q'_1}{Q'_2} = \frac{Q_1}{Q_2} = \frac{R_2}{R_1}.$$

With a very low resistance branch point, that is, such that $\Delta \ll R_1, R_2$, we have on the other hand:

$$\frac{Q'_1}{Q'_2} = \frac{Q_1}{Q_2} = \frac{r_2}{r_1}$$

In consequence, if there are more drops in the section $r_1$ than in the section $r_2$, we obtain $r_1 > r_2$ and hence $Q_1' > Q_2'$, which tends to direct the next drop to the second branch.

It should also be observed that the mechanism is fairly independent of what happens downstream, beyond the bypass. If in fact we derive the expression of the ratio of the outlet flow rates respectively with regard to $r_2$ and $R_2$, we obtain:

$$\frac{d}{dr_2}\left(\frac{Q'_1}{Q'_2}\right) = \frac{(\Delta + R_1 + R_2)}{r_1(\Delta + R_1 + R_2) + \Delta R_1}$$

and $$\frac{d}{dR_2}\left(\frac{Q'_1}{Q'_2}\right) = \frac{\Delta}{r_1(\Delta + R_1 + R_2) + \Delta R_1}$$

Assuming the case $\Delta \ll R_1, R_2$, and assuming branches to be balanced, actually because of $R_1 = R_2 = R$ and $r_1 = r_2 = r$, we accordingly have:

$$\frac{d}{dr_2}\left(\frac{Q'_1}{Q'_2}\right) = \frac{2}{2r + \Delta}$$

and $$\frac{d}{dR_2}\left(\frac{Q'_1}{Q'_2}\right) = \frac{\Delta}{(2r + \Delta)R}$$

thus, $$\frac{\frac{d}{dr_2}\left(\frac{Q'_1}{Q'_2}\right)}{\frac{d}{dR_2}\left(\frac{Q'_1}{Q'_2}\right)} = \frac{2R}{\Delta} \gg 1$$

which means that the increase in the hydrodynamic resistance of a branch caused by the presence of a given drop in this branch will have a negligible effect on the flow rate distribution at the junction, once this drop has passed the branch point.

Details of the Invention

1) Design of the Channels

A Y intersection geometry can be selected, in which the two daughter branches, that is the branched channels, form a right angle. If the inertial effects are normally negligible, it is nevertheless observed that a T configuration favors a stagnation of the drops issuing from the parent flow channel at the junction, thereby favoring coalescence. In contrast, the Y configuration visibly reduces the time taken by the drops to decide for one or the other of the daughter branches.

Figure 8:
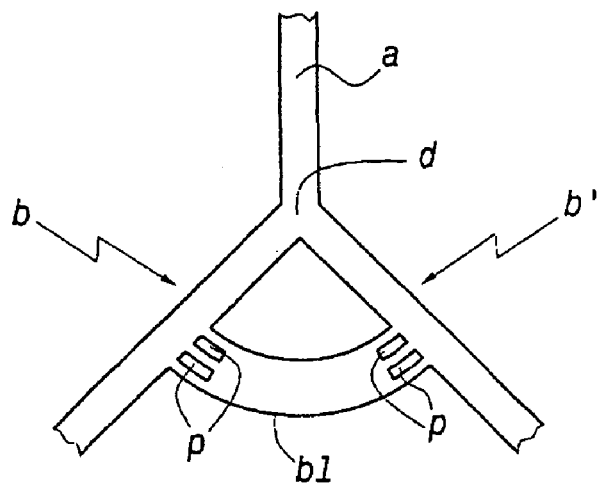
FIG. 8 is a front view, similar to FIG. 1, showing an alternative embodiment of the invention.

A linking channel (bypass) is added to this intersection model, the arrangement indicated in FIG. 8 satisfying both the conditions mentioned previously and clearly shown. This arrangement is an example and is nonlimiting. It shows a parent flow channel a, two branched channels b and b' connected by a linking channel bl, defining a branch point d.

The cross section of the linking channel is similar to that of the two branched channels. However, at its two ends, that is close to its intersection with each of these branched channels, this linking channel has a cross section substantially lower than that of the abovementioned branched channels.

For this purpose, two pairs of studs p, forming obstacles, are provided close to the intersection of the linking channel and of each of the branched channels. However, as an alternative, other means can be considered for locally reducing the cross section of this linking channel. Thus, as a nonlimiting example, the latter can be provided with two bottlenecks, at each of its ends.

2) Dimensioning of the Bypass

The width of the channels may, for example, be 150 μm.

The dimensions of the bypass can be selected as follows.

Figure 9:
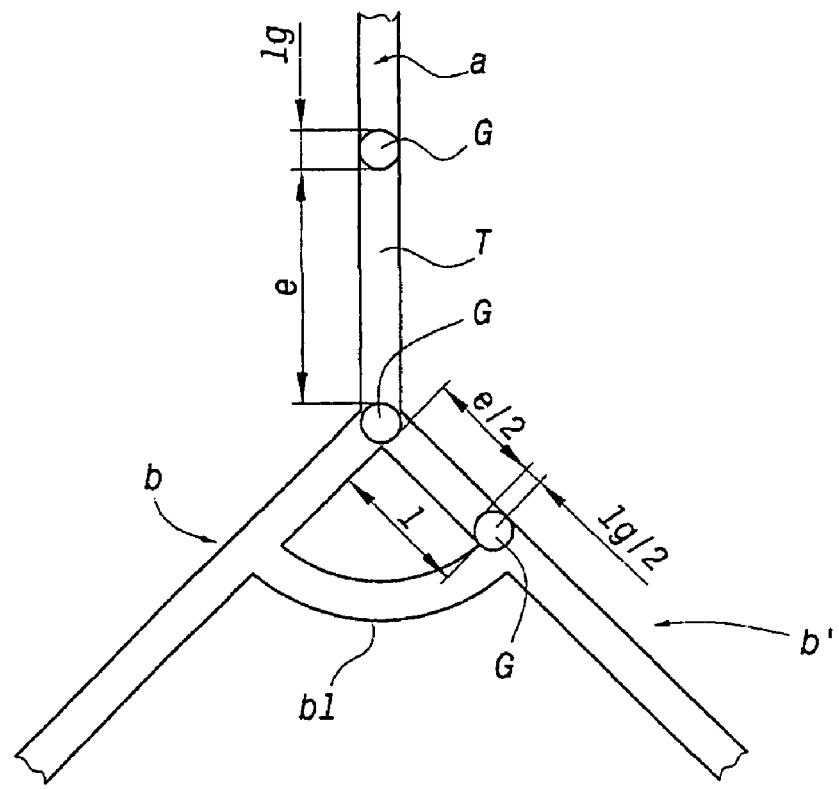
FIG. 9 is a front view, similar to FIG. 1, showing the implementation of the device shown in FIG. 8.

For the branch point to operate optimally, it is preferred, whenever a drop reaches an intersection, that the preceding drop has not yet passed the branch point. With reference to FIG. 9, if lg denotes the length of a drop and e the edge-to-edge spacing measured between two drops, a first condition is identified on the length l of the short-circuit network branch brc, comprised in consequence between the intersection and the branch point.

As the oil spreads equally between the two branches in a balanced tree structure, the edge-to-edge distance between the drop at the junction and the one that will soon pass the branch point is equal to half of the initial spacing e between these drops. For the bypass to operate optimally, it is therefore preferable to have a length l greater than the sum $e/2 + lg/2$, without which the downstream drop no longer plugs the channel and no longer has such an important effect on the other.

Furthermore, it may be desirable to operate with drops that are sufficiently distant to limit coalescence mechanisms if such mechanisms are undesirable. For this purpose, l can be selected so that there is only one drop between the intersection and the branch point in any given branch. This is guaranteed when the penultimate drop passed has passed the branch point, that is, when $e + lg$ is higher than l.

In brief, it may be preferable to determine l in order to have $(e + lg)/2 < l < e + lg$.

In fact, the drops handled generally have a length of at least 150 μm so that they occupy the entire width of the channel and do not follow the current lines without necessarily exceeding the Rayleigh-Plateau limit, that is, p.w where w denotes the width of the channel, without which they would break at all the intersections regardless of their speed. The typical size of the drops can therefore be about 200 μm. As to the spacing, it is preferably at least equal to the length of a drop.

The length l can be set at 450 μm. Unless the situation is that of small drops close together, one can thus avoid having too many drops between the junction and the branch point. This choice may also serve to vary the spacing up to five times the length of a drop (for the smallest).

Figure 10:
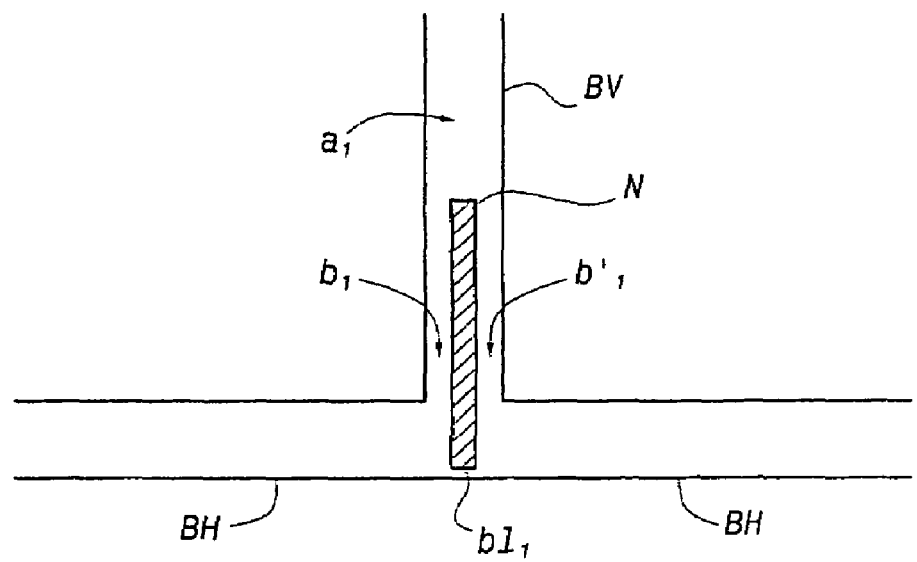
FIG. 10 is a front view, similar to FIG. 8, showing an additional alternative embodiment of the invention.

FIG. 10 shows an additional alternative embodiment of the invention. This figure shows a T shaped arrangement, thus having a vertical branch BV and two horizontal branches BH, with reference to this figure.

The end of the vertical branch, adjacent to these horizontal branches, is provided with a rib N which corresponds for example to an unetched part of the plate, in which the channels are prepared.

This rib N thereby serves to define two branched channels $b_1$ and $b'_1$ in the context of the invention, whereof each comprises the end of the vertical branch, located below the insert, and a corresponding horizontal branch. Moreover, the lower end of the rib defines, with the wall opposite the horizontal branches, a linking channel $b_1$ according to the invention, whereas the flow channel $a_1$ is formed by the upper part of the vertical branch.

The dimensions of the rib N are such that the branched channels $b_1$ and $b'_1$ allow the passage of plugs, such as drops. In contrast, this rib N is sufficiently close to the walls opposite the horizontal branches BH, so that the linking channel $bl_1$ has dimensions such as to prevent the passage of these plugs along this linking channel.

3) Bypass Operating Diagram

The presence of the linking channel belonging to the "bypass" of the invention can lead to the following types of operation:

a) Drop Breakage

Figure 11:
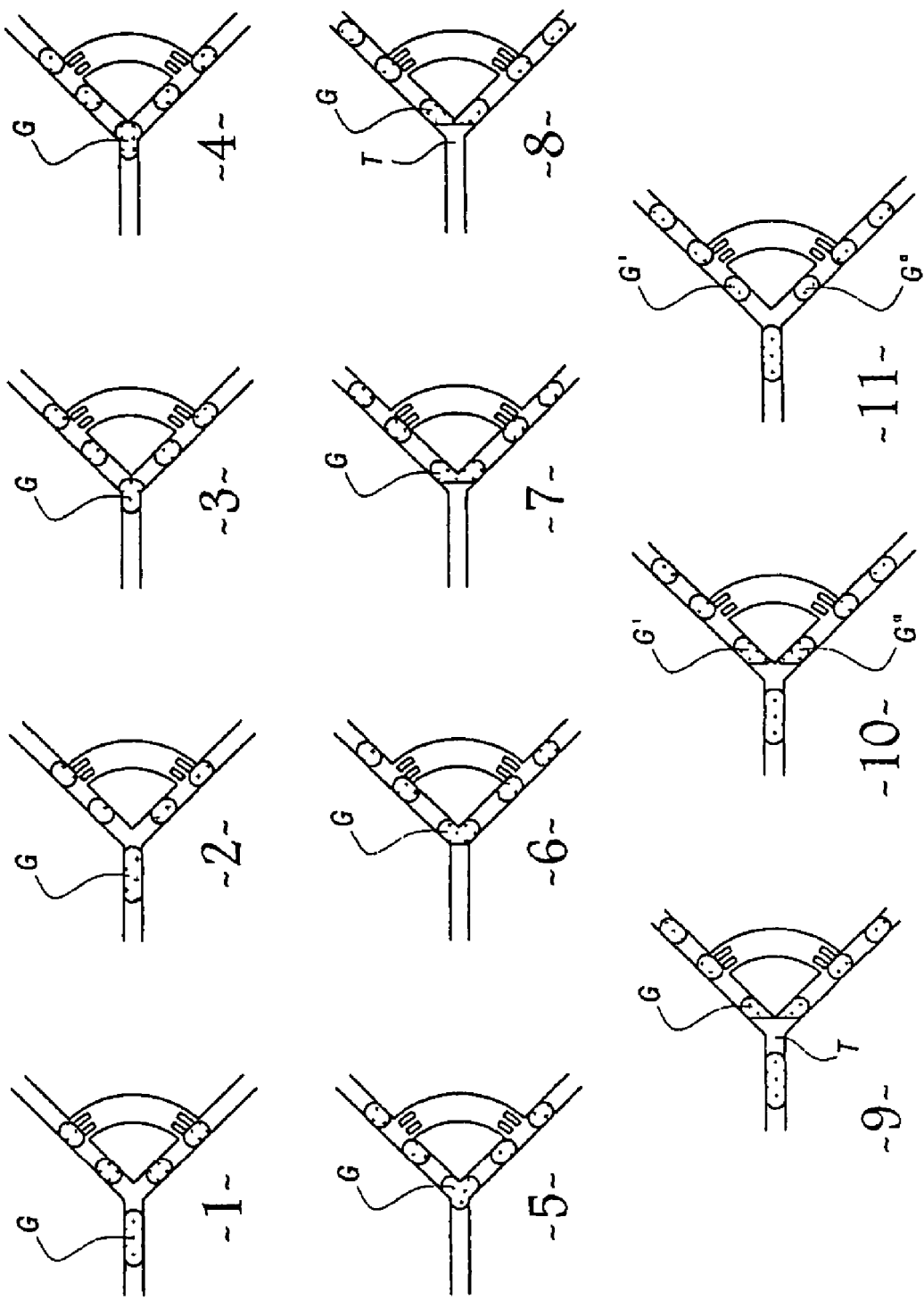
FIGS. 11 to 13 are series of pictures, showing the advance of the drops in the device in FIG. 8.

A number of drops, particularly the biggest or, otherwise, the smallest but reaching the junction at high speed, may break into two smaller drops at the intersection or junction, or branch point. The pictures in FIG. 11 show the various steps of this occurrence for a divergent type of flow mode: the drop G emerges in the intersection and flattens (photos 1 to 4), and then changes its main axis and spreads vertically (photos 5 to 7). The stream of carrier fluid T (for example a fluid such as oil) from upstream then crushes the drop on the apex of the junction (photos 8 and 9) progressively reducing its width until it breaks, thereby giving rise to two drops G' and G" which are smaller (photos 10 and 11).

The breaks may in particular occur in a divergent type of flow mode.

b) Distribution at a Uniform Rate

Figure 12:
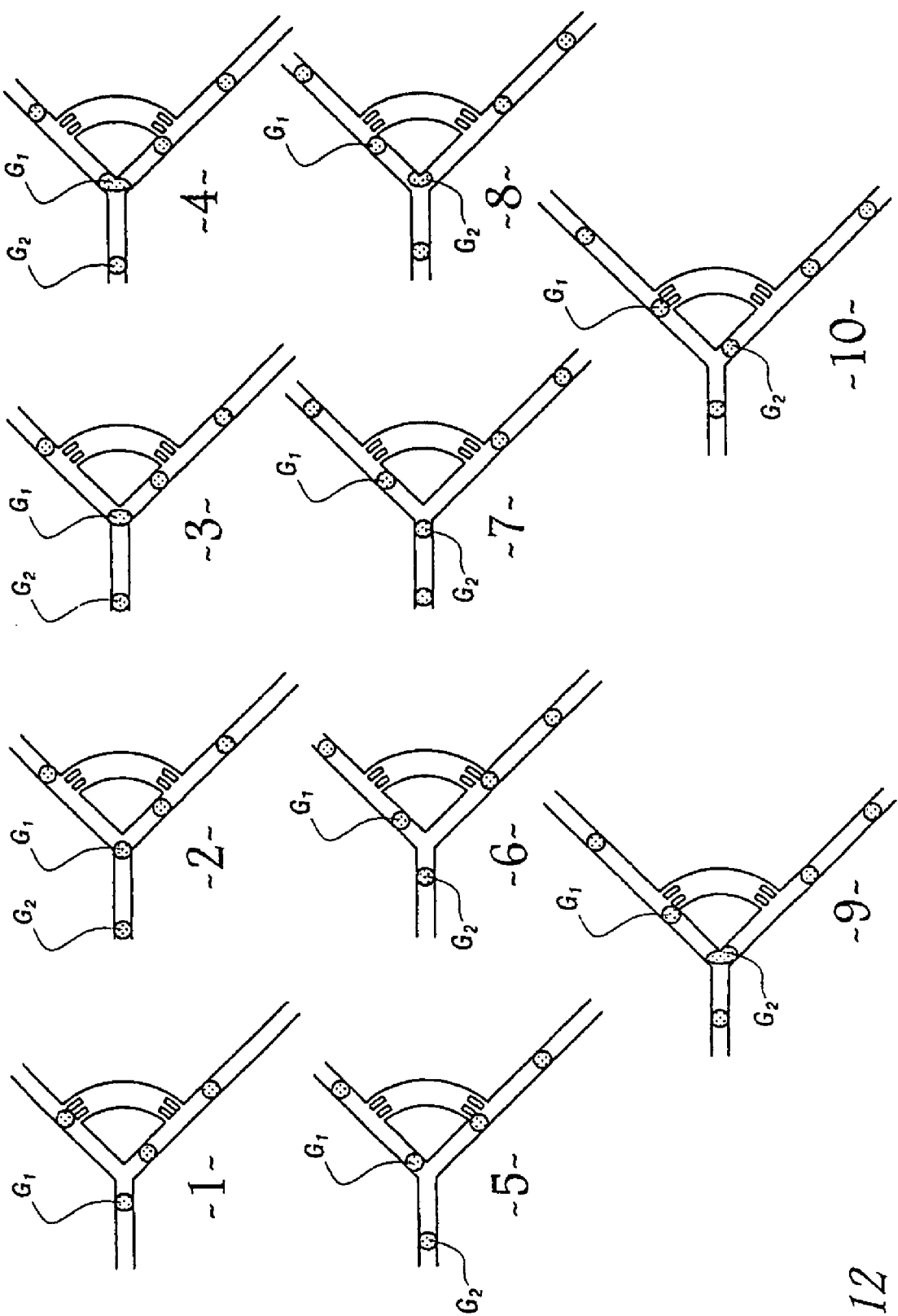

This condition can be characterized by ideal operation of the bypass: two successive drops $G_1$ and $G_2$ systematically decide to continue their route in a different branch at the intersection. The photos in FIG. 12 show the various steps of this strict alternation in the distribution of the drops for a divergent type of flow mode.

The distribution at a uniform rate can in particular occur in a divergent type of flow mode.

c) Coalescence

Figure 13:
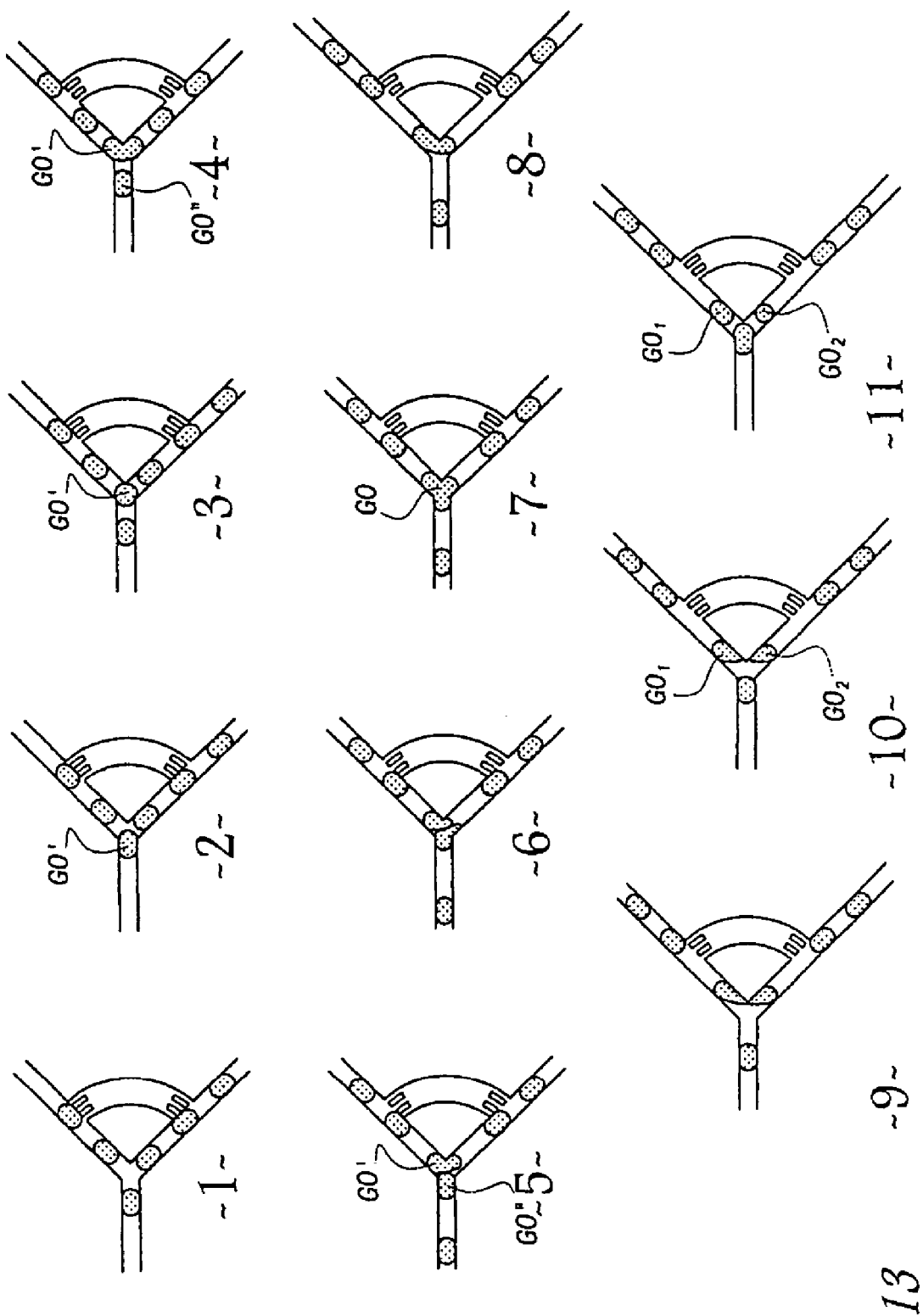

In a number of cases, coalescences at the junction may also be observed. These coalescences cause such an extension of the drop that they may be followed by a break of the drop. The photos in FIG. 13 show the various steps of coalescence followed by breakage for a divergent type of flow mode. Thus, the two initial drops GO' and GO" coalesce to form a single drop GO, which then breaks into two drops $GO_1$ and $GO_2$.

The coalescence may in particular occur in a divergent type of flow mode. It may also be a convergent type of operating mode. For divergent type operating modes, the coalescence may be a preferred mode of embodiment.

According to an advantageous embodiment, in convergent flow mode, ratios (drop spacing)/(bypass length l) between 1 and 2 are used. This mode is particularly preferred to implement a distribution at a uniform rate 1-1.

Without being tied to a theory, it is believed that this distribution is explained as follows: if a drop is separated in the flow channel A by a distance e from the one preceding it before the branch point, or junction, or intersection, once it has reached the branch point, it is no longer at a distance e/2 from it if the volume of carrier fluid between these two drops is equally distributed between the two branched channels, for example because of a balancing of the tree structure. When the spacing e between the drops has a bypass length l (e=l), the drop reaching the branch point finds the preceding drop at the middle of one of the two branches of the bypass and sees the one in front exit the other branch of the bypass at this precise moment. The bypass can accordingly operate and cause the flow of the drop into the now liberated branch. When the spacing has two bypass lengths (e=2*l), the drop reaching the junction sees the preceding drop on the verge of exiting from a branch of the bypass but still blocking this branch, while the drop in front has passed the branch point long ago. The bypass can still operate and send the drop into the branch free of any drop.

According to another embodiment, in convergent flow mode, ratios (drop spacing)/(bypass length l) of around 0.5 are used. This implies exactly enough space for two drops in a branch of the bypass and, if the speed is not too high, a good flow condition is obtained with one drop alternatively to left and to right.

According to another embodiment in convergent flow mode, ratios (drop spacing)/(bypass length l) lower than 0.5 are used, preferably with flows at relatively low speed. In this embodiment, coalescence predominates.

Without being tied to a theory, it is believed that this is explained as follows: the risk of coalescence is greater when the drops are close together but a low speed then also has an effect because in this case, the drops, which roll over one another when in a condition of promiscuity, will be in contact for even longer the slower they are. The carrier fluid which separates them and momentarily prevents their coalescence thereby has the time to be removed and the drops can coalesce.

When the speed is increased and for longer spacings, the drops tend more to break. Increasing the speed causes a greater extension of the drop at the intersection, increasing the risk of a break as described in the first part of the description.

Figure 14:
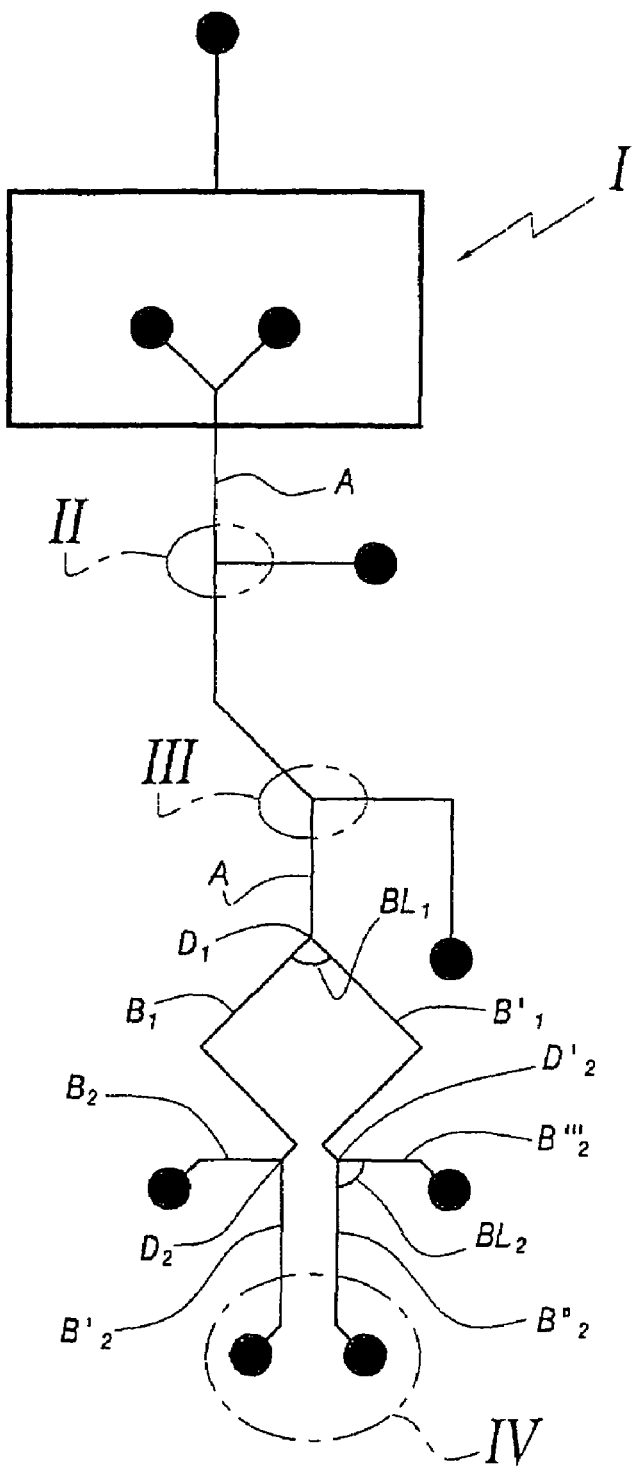
FIG. 14 is a schematic view, showing a microfluidic flow device according to an additional alternative embodiment of the invention.

With reference to FIG. 14, we can now evaluate the effectiveness of the bypass by comparing the outlet of a "bypassed" junction with that of a non "bypassed" junction when they are fed with the same type of drops, in terms of size, spacing and speed.

This FIG. 14 shows a flow channel A, placed downstream of a zone I, for producing drops in a manner known per se. In consequence, this channel A receives a succession of drops and sections of carrier phases, as shown in FIG. 3.

Then, in a zone II, oil is added in a manner known per se, in order to separate these drops and, in a zone III, these drops are broken, in a manner also known per se. This flow channel A accordingly flows into a first branch point $D_1$, downstream of which two branched channels are found in the sense of the invention, denoted $B_1$ and $B'_1$, which are connected by a linking channel $BL_1$.

The branched channel $B_1$ flows in its turn into a second branch point $D_2$, downstream of which two $2^{nd}$ order branched channels $B_2$ and $B'_2$ are found. However, it may be observed that these two branched channels are not connected by a linking channel, in the sense of the invention. The other $1^{st}$ order branched channel $B'_1$ flows into a $2^{nd}$ order branch point $D'_2$, downstream of which two other $2^{nd}$ order branched channels are found, denoted $B''_2$ and $B'''_2$. It should be observed that the latter are connected by a $2^{nd}$ order linking channel $BL_2$, contrary to the other branched channels $B_2$ and $B'_2$.

The two branched channels $B'_2$ and $B''_2$, whereof the first has not undergone a "bypass" in the sense of the invention, and whereof the other has undergone a "bypass" in the sense of the invention, extend adjacently into an observation zone IV, which can be observed using an appropriate camera.

This observation demonstrates the effectiveness of the bypass of the invention. Thus, in the bypassed branched channel $B''_2$, a nearly perfect 1:1 distribution is obtained, whereas trains of drops flow in the non-bypassed channel $B'_2$.

The microfluidic flow device according to the invention can, in a manner not shown, be provided with means for analyzing the various fluids flowing therein, particularly the plugs., These analytical means may be optical, particularly a Raman analyzer, or infrared or even fluorescence type. This device may also comprise means for imposing a gradient of at least one operating condition, in at least one branched channel.

In an equivalent manner not shown, analyses of the various plugs can be performed, particularly when they are formed from a mixture, in branched channels of different orders. Based on this analytical step, it is possible, for example, to determine the kinetic parameters of the conversion occurring between the components of the plugs, particularly a kinetic constant. In the case in which, as mentioned above, a gradient of at least one operating condition is applied, it is possible to detect the appearance of crystals or different spatial arrangements in the branched channels subjected to this gradient. In this case, it is possible to determine a solubility diagram or a phase diagram.

The invention claimed is:

1. A microfluidic flow device comprising:
   at least one flow channel flowing into a first branch point to which at least two branched channels are connected, said branched channels having respective lengths, and
   at least one linking channel interconnecting the two branched channels,
   the linking channel flowing into each branched channel at a respective short-circuit point located intermediate the ends of respective lengths of the branched channels at less than half of the length of each branched channel starting from the first branch point,
   at least one of the branched channels of the first branch point flowing into a second branch point to which at least two branched channels are connected, the branched channel extending between the two branch points constituting a branched channel of the first branch point and a flow channel of the second branch point.

2. The device as claimed in claim 1, characterized in that it comprises a linking channel interconnecting the two branched channels of the second branch point and flowing into each branched channel of the second branch point at a respective short-circuit point located at less than half of its length from each branched channel.

3. The device as claimed in claim 1, wherein said at least two branched channels constitute at least two 1st order branched channels, whereof at least one is divided at the second branch point into at least two 2nd order branched channels, at least one (n-1th) order branched channel being divided at an nth branch point ($D_n$) into at least two nth order branched channels ($B_n$, $B'_n$), n being greater than or equal to 2, preferably 4, and preferably to 7.

4. The device as claimed in claim 3, characterized in that each $i^{th}$ order branch point, where i=1 to n, is associated with one $i^{th}$ order linking channel ($BL_i$).

5. The device as claimed in claim 1 wherein the channels constitute a tree structure like system, the tree structure like system being symmetrical or asymmetrical.

6. The device as claimed in claim 5, characterized in that the flow channel and the branched channels constitute a symmetrical tree structure like system.

7. The device as claimed in claim 5, characterized in that the flow channel and the branched channels constitute an asymmetrical tree structure like system.

8. The device as claimed in claim 1, wherein the linking channel is provided with cross section reducing means for locally reducing its cross section.

9. The device as claimed in claim 1 wherein the linking channel comprises studs partially plugging the fluid inlet into said linking channel.

10. The device as claimed in claim 1, further comprising means for generating mobile fluid plugs separated by a carrier fluid, the plug fluid and the carrier fluid being immiscible.

11. The device as claimed in claim 1, wherein it is a divergent device, the flow channel being connected to a fluid inlet, the branched channels being connected to fluid outlets.

12. The device as claimed in claims 10, wherein it is a divergent device, the flow channel being connected to a fluid inlet, the branched channels being connected to fluid outlets, and further wherein the flow channel is connected to said plug generating means.

13. The device as claimed in claims 1, wherein it is a convergent device, the flow channel being connected to a fluid outlet, the branched channels being connected to fluid inlets.

14. The device as claimed in claims 10, wherein it is a convergent device, the flow channel being connected to fluid outlet, the branched channels being connected to fluid inlets, and further wherein at least one of the branched channels, preferably at least both, is/are connected to the plug generating means.

15. A method for sending or controlling material streams comprising the following steps:
   introducing a fluid into at least one inlet of the device claimed in claim 1, and
   creating a fluid flow, divergent or convergent, through the flow channel and the branched channels, wherein the fluid flow in the branched channels communicates with the linking channel at said locations intermediate the ends of the respective lengths of the branched channels.

16. The method as claimed in claim 15, characterized in that the fluid comprises mobile fluid(s) plugs, or drops or dispersed entities, separated by a carrier fluid, the plug fluid and the carrier fluid being immiscible.

17. The method as claimed in claims 16, wherein the plugs in the fluid upstream of the branch point are spaced at regular intervals.

18. The method as claimed in one of claims 15 to 17, characterized in that:
   the fluid is introduced at an inlet connected to the flow channel,
   the fluid flow comprising the plugs and the carrier fluid in the channel is a divergent flow from the fluid inlet in the flow channel to the branch point, and from the branch point to the branched channels,
   at the branch point the plugs:
   are distributed at a substantially uniform rate in one branched channel then to the other,
   are divided into two divided plugs, and/or coalesce with at least one of the next plugs.

19. The method as claimed in one of claims 15 to 17, characterized in that:
   two fluids comprising plugs, identical or different, are introduced at two inlets each connected to a branched channel,
   the fluid flow comprising the plugs and the carrier fluid in the channel is a convergent flow, from the fluid inlet in the branched channels to the branch point, and from the branch point to the flow channel, at the branch point at least one plug from a branched channel coalesces with at least one plug from the other branched channel.

20. The method as claimed in claim 15 which is implemented in operations for preparing or creating materials or for measuring properties.

21. The method as claimed in one of claims 16 characterized in that the plugs in the flow channel comprise a mixture of compounds, preferably mixed upstream of the plug formation, or during the plug formation in a convergent device, and/or mixed in the branch points during a coalescence.

* * * * *

UNITED STATES PATENT AND TRADEMARK OFFICE
CERTIFICATE OF CORRECTION

PATENT NO. : 7,691,331 B2  Page 1 of 1
APPLICATION NO. : 11/518437
DATED : April 6, 2010
INVENTOR(S) : Armand Ajdari It is certified that error appears in the above-identified patent and that said Letters Patent is hereby corrected as shown below:

Title Page, insert, --(63) Related U.S. Application Data:
Provisional application no. 60/738,033, filed on November 21, 2005--.

Signed and Sealed this

Thirtieth Day of November, 2010

David J. Kappos
*Director of the United States Patent and Trademark Office*